United States Patent [19]

Okayama et al.

[11] Patent Number: 5,800,809
[45] Date of Patent: *Sep. 1, 1998

[54] NON-CROSSLINKED ACRYLIC POLYMERS AND NON-CROSSLINKED ANION EXCHANGE RESINS

[75] Inventors: Minenobu Okayama; Shuji Sato, both of Tsukuba, Japan

[73] Assignee: Hisamitsu Pharmaceutical Co, Inc, Tosu, Japan

[*] Notice: The term of this patent shall not extend beyond the expiration date of Pat. No. 5,665,348.

[21] Appl. No.: 816,844

[22] Filed: Mar. 13, 1997

Related U.S. Application Data

[63] Continuation-in-part of Ser. No. 256,486, Jul. 8, 1994, Pat. No. 5,665,348.

[30] Foreign Application Priority Data

Jan. 14, 1992 [JP] Japan ............................ 4-24531

[51] Int. Cl.⁶ .................................. A61K 31/785
[52] U.S. Cl. ........................ 424/78.12; 424/78.35; 526/310
[58] Field of Search ................... 424/78.16, 78.01, 424/78.12, 78.35

[56] References Cited

U.S. PATENT DOCUMENTS

| 3,239,496 | 3/1966 | Jursich | 526/312 |
| 3,661,880 | 5/1972 | Markert et al. | 526/312 |
| 5,665,348 | 9/1997 | Okayama et al. | 424/78.35 |

FOREIGN PATENT DOCUMENTS

| 61-138607 | 6/1986 | Japan | 526/312 |
| 62-270609 | 11/1987 | Japan | 526/312 |
| WO9118027 | 11/1991 | WIPO | 424/78.12 |

*Primary Examiner*—Peter F. Kulkosky
*Attorney, Agent, or Firm*—Bucknam and Archer

[57] ABSTRACT

The present invention provides a non-crosslinked acrylic polymer and a non-crosslinked anionic exchange resin consisting of polyacryloyloxyethyl-N,N-dimethylbenzyl ammonium salt.

8 Claims, 3 Drawing Sheets

Dose-Response Curves of the Suppression of Increase in Cholesterol Level

Infrared Absorption Spectrum of the Non-Crosslinked Polymer

Dose-Response Curves of the Suppression of Increase in Cholesterol Level

Infrared Absorption Spectrum of the Non-Crosslinked Polymer

Effect of HBS-107 on total cholesterol level in WHHL rabbits
*;p<0.05,**;p<0.01 vs. control (Student's t test)

NON-CROSSLINKED ACRYLIC POLYMERS AND NON-CROSSLINKED ANION EXCHANGE RESINS

This application is a continuation in part on Ser. No. 08/256,486 filed Jul. 8, 1994 and now U.S. Pat. No. 5,669, 348.

This invention relates to a non-crosslinked acrylic polymer and non-crosslinked anion exchange resin each consisting of polyacryloyloxyethyl-N,N-dimethylbenzyl ammonium salt.

BACKGROUND OF THE PRIOR ART

It has been known that lowering a blood cholesterol level is effective in preventing atherosclerosis. In particular, the investigation conducted by U.S. Lipid Research Clinics Program has clarified that a decrease in blood cholesterol level correlates to the suppression of the incidence of cardiac coronary arterial diseases and that anion exchange resins are effective in preventing these diseases. Anion exchange resins which are publicly known to have been used as a cholesterol-lowering drug for lowering a blood cholesterol level, are for example cholestyramine which is a polymer of styrylmethyltrimethylammonium chloride, and a composition containing styrylmethyltrimethylammonium chloride (see U.S. Pat. Nos. 3,499,960 and 3,780,171 and Japanese Patent Laid-Open Gazette No. 10386/78). Further, a copolymer of imidazole with halomethyloxysilane, having a higher efficacy than cholestyramine, has been reported as another example (see Japanese Patent Laid-Open Gazette No. 124819/90). Furthermore, Japanese Patent Laid-Open Gazette No. 212505/90 discloses an acrylic polymer containing a quaternized alkylammonium and a composition comprising the polymer as still other examples. However, the exchange capacity (from 1.98 to 3.66 meq $Cl^-$/g) disclosed in this Gazette cannot be thought to be sufficiently large as compared with that of cholestyramine (2.9 meq $Cl^-$/g; see U.S. Pat. No. 3,780,171). The compound disclosed in the Japanese Patent Laid-Open Gazette No. 212505/90 cited above involves a crosslinking unit as an essential constituent factor. Accordingly, this Gazette has neither disclosed nor suggested that non-crosslinked acrylic polymers and non-crosslinked anion exchange resins disclosed in the present invention have an effect of lowering a cholesterol level.

It is believed that these acrylic polymers and anion exchange resins adsorb and fix bile acids thereto and thus promote the catabolism of cholesterol into bile acids to lower the blood cholesterol level as will be discussed in greater detail hereinafter.

Bile acids are synthesized from cholesterol serving as a precursor thereof in the liver, secreted from the common bile duct into the intestinal tract, absorbed together with fat-soluble substances and then recovered into the liver, thus circulating through the bowels and the liver. Therefore, bile acids are present in a fixed amount in the cycle called the enterohepatic circulation without their systemic circulation (bile acid pool). When bile acids are bonded to an acrylic polymer or an anion exchange resin in the intestinal tract and evacuated, the amount of bile acids pooled is reduced. As a result, cholesterol 7 α-hydroxylase is activated in hepatic cells and thus bile acids are biosynthesized. Then the cholesterol concentration in the liver is lowered. To make up for the decreased cholesterol concentration, LDL (low density lipoprotein) receptor appears on hepatic cell membranes and thus LDL cholesterol in the blood is recovered or withdrawn into the liver. As a result, the blood cholesterol level is lowered. It is believed that the acrylic polymer or anion exchange resin exerts the effect of lowering cholesterol level through the mode of action as described above.

Typical of drugs for treating hypercholesterolemia which are known today are as follows. For example, cholestyramine has been widely used in a clinic as a priority drug for treating familial hypercholesterolemia; however, it has a disadvantage that it adsorbs fat-soluble vitamins under the influence of hydrophobic interaction, thereby making it necessary to supply fat-soluble vitamins such as vitamins K and D to make up for the loss thereof in the case of the prolonged administration of cholestyramine. In addition, conventional cholesterol-lowering drugs including cholestyramine preparations are inconvenient in that they should be suspended before use. Cholestyamine has another disadvantage that a patient is forced to take a large dose (8 to 16 g per day) because of its poor capability of adsorbing bile acids, thus inflicting a burden to the patient. Furthermore, it is known that a cross-linked polymer is expanded in volume through swelling. This is sometimes clinically observed as side effects including abdominal swelling and constipation. Furthermore, a still another disadvantage is that some patients will not take the drug as directed by the doctor because of said problems raised at the time of administration of the above conventional drugs.

As an existing technique for solving the above-mentioned problems, Sugii et al. of Kumamoto University introduced an ω-oxobutyl chain as a spacer between an aliphatic quaternary ammonium salt and a main polystyrene chain and thus improved the accessibility of bile acids to an ion exchange group and the hydrophobic interaction of the spacer to enhance the adsorption affinity, thus increasing the amount of bile acids discharged in feces [see J. Pharmacobio-Dyn., 13, 130–135 (1990)]. However, this ion exchange resin has a still low bile acid adsorptivity and therefore it exerts only an insufficient effect of lowering the blood cholesterol level.

On the other hand, existing water-soluble quaternized polymers such as cationized cellulose will highly irritate the mucosae when used and thus they do not satisfy the practical usefulness as a drug for internal use.

SUMMARY OF THE INVENTION

It is an object of the present invention to provide a non-crosslinked acrylic polymer including a non-crosslinked anion exchange resin and used, for example, in a cholesterol-lowering drug which can be easily taken in the form of, for example, tablets, granules and capsules, which relieves side effects such as abdominal swelling and constipation experienced in the conventional cholesterol-lowering drugs containing cross-linked ion exchange resins, which overcomes their disadvantages of adsorbing fat-soluble vitamins and forcing a patient to have a large burden at the time of their administration and which eliminates the inconvenience that they must be suspended before use.

The present inventors have conducted extensive studies in order to solve the above-mentioned problems. As a result, they have found: (1) that by replacing an alkyl group of an aliphatic quaternary ammonium salt of a non-crosslinked acrylic polymer or an anion exchange resin by, for example, a benzyl group, the selective adsorption of bile acids can be enhanced and the mucosal irritation can be relieved as compared with the existing anion exchange resins; (2) that by using a linear resin, the effective amount of bile acids adsorbed per unit weight of resin can be increased; and (3)

that the larger the amount of bile acids adsorbed per unit weight of resin is, the more the blood cholesterol level is reduced. The present invention has been completed based on these findings.

The present invention relates to a non-crosslinked acrylic polymer and non-crosslinked anion exchange resin which is formed from the polymer, each consisting of polyacryloyloxyethyl-N,N-dimethylbenzyl ammonium salt.

Now, the non-crosslinked acrylic polymer and non-crosslinked anion exchange resin according to the present invention will be described in greater detail.

The counter ions which form a salt in polyacryloyloxyethyl-N,N-dimethylbenzyl ammonium salt can be physiologically acceptable ones. Among these counter ions, a sulfate or phosphate ion, or a halide ion such as $Cl^-$ or $Br^-$ is particularly preferable.

The polymerization degree of the polyacryloyloxyethyl-N,N-dimethylbenzyl ammonium salt in the present invention is from about 10 to about 20,000. When the polymerization degree is less than 10, the adsorption property of bile acids is unfavorably deteriorated since this compound is easily excreted even in a case where it is administered to a patient in a predetermined dose. On the other hand, when the polymerization degree thereof is more than 20,000, the adsorption property of bile acids is unfavorably deteriorated since this compound will increase very highly in viscosity.

There is preferably used a cholesterol-lowering drug comprising, for example, a non-crosslinked anion exchange resin, formed from the polymer non-crosslinked acrylic polymer, of the present invention. This non-crosslinked acrylic polymer or non-crosslinked anion exchange resin has, as its essential properties, not only a pH of about 4.5 to about 6.5 when 0.5 g of the polymer are dissolved in water to obtain 50 ml of a solution thereof but also a viscosity of not more than about 150 centipoise when the polymer is dissolved in water to form a 1 wt. % aqueous solution at 25° C.

The anion exchange resins of the present invention within said range of pH or viscosity exhibit a higher saturated amount of bile acids and superior when used as a cholesterol-lowering drug than those which are beyond the range.

Now a preferable example of a method for producing a non-crosslinked acrylic polymer of the present invention will be described. For example, the preferable method for producing the acrylic polymer wherein a benzyl group is introduced as $R_1$ may generally be effected in the following manner. An unsaturated N,N-dimethylamine such as acryloyloxyethyl-N,N-dimethylamine of formula $CH_2=CHCOO(CH_2)_2-N(CH_3)_2$ is reacted with an aralkyl halide such as benzyl chloride or benzyl bromide in an organic solvent such as acetone, methanol, ethanol, diethyl ether or isopropyl ether. The quaternary monomer thus obtained is subjected to free-radical polymerization in accordance with the conventional method in water or a polar solvent such as ethanol or methanol within a reaction temperature of from about 15° to about 80° C. in the presence of a free-radical initiator such as azobisisobutyronitrile (AIBN) or an ammonium persulfate redox initiator (for example, ammonium persulfate/sodium hydrogensulfite) for a reaction time of from about 0.5 to about 30 hours. The reaction product is precipitated from an appropriate organic solvent such as acetone or dioxane and dried by air-drying, vacuum-drying, spray-drying or freeze-drying to thereby give an anion exchange resin.

When the anion exchange resin which is formed from the non-crosslinked acrylic polymer which is the compound of the present invention is to be used in therapeutics, it is generally employed in the form of a drug composition. When the anion exchange resin of the present invention is used in the preparation of a drug composition, the resin is preferably a synthesized one which is at least 99% by weight in purity. Thus a drug composition is prepared by incorporating the anion exchange resin which is formed from the non-crosslinked acrylic polymer, with pharmacologically acceptable vehicles or excipients.

The drug composition using therein the anion exchange resin which is formed from the non-crosslinked acrylic polymer of the present invention can be formulated into, for example, tablets, granules, dusts, capsules, syrups, emulsions, suspensions or solutions by a publicly or well known method. For example, a solid preparation in the form of tablets or granules can be obtained by appropriately blending with the excipients, for example, sugars such as lactose, sucrose, glucose, mannitol or sorbitol, starches such as corn starch, potato starch or dextrin, microcrystalline cellulose, gum arabic, dextrin, pullulan, light silicic anhydride, aluminum silicate, magnesium metasilicate aluminate, magnesium silicate, calcium phosphate, calcium carbonate or calcium sulfate, disintegrating agents such as carboxymethylcellulose, carboxymethylcellulose sodium, carboxymethylcellulose calcium, hydroxypropylcellulose, crystalline cellulose, ethylcellulose, carboxymethylstarch sodium or croscarmellose sodium, binders such as polyvinylpyrrolidone, polyvinyl alcohol or hydroxypropylcellulose, lubricating agents such as talc, stearic acid, magnesium stearate or calcium stearate, and other components such as polyethylene glycols, propylene glycol and coloring matters.

To formulate preparations for use in the capsuled form, there may be appropriately blended together base materials for a hard or soft capsule which are gelatin, glycerol, sorbitol, propylene glycol, sucrose, a plasticizer such as gum arabic, a pigment and a coloring matter such as titanium dioxide, a preservative such as methyl, ethyl or propyl p-hydroxybenzoate (parabens), perfume and other excipients.

To formulate preparations in the form of syrups, emulsions, suspensions and solutions, there may be blended together solubilizers or emulsifiers such as water, ethanol, nonionic surfactants such as glycerol, sorbitol, polyethylene glycol, propylene glycol, glycerol monostearate, polyoxyl stearate, lauromacrogol, sorbitan oleate, polysorbate 80 and sucrose fatty acid esters, anionic surfactants such as stearyltriethanol-amine and sodium lauryl sulfate, cationic surfactants such as benzalkonium chloride and benzethonium chloride, ampholytic surfactants such as lecithin, suspending agents or dispersing agents such as the nonionic, anionic and cationic surfactants as cited above, polyvinyl compounds such as polyvinyl alcohol and polyvinylpyrrolidone, cellulose derivatives such as carboxymethylcellulose sodium, methylcellulose, hydroxymethylcellulose, hydroxyethylcellulose, hydroxypropylcellulose and hydroxypropylmethyl-cellulose, other materials such as gum arabic and gelatin, thickening agents such as aluminum magnesium silicate, colloidal hydrous aluminum magnesium silicate, bentonite, kaolin and microcrystalline cellulose, preservatives such as parabens, benzalkonium chloride and benzethonium chloride, flavors and sweeteners such as fructose, invert sugars, cocoa, citric acid, ascorbic acid and fruit juices, and other excipients.

Each preparation thus obtained is formulated into a unit dose form containing from 0.01 to 3.0 g of the anion exchange resin obtained by the present invention.

This preparation can be administered to a patient in a dose of from 0.1 to less than 8 g/day, preferably from 0.5 to 7 g/day, more preferably from 1 to 5 g/day, once to thrice per day. It is necessary to repetitively administer the preparation for at least a period of time sufficient for causing a decrease in the serum cholesterol level. [

Figure 1:
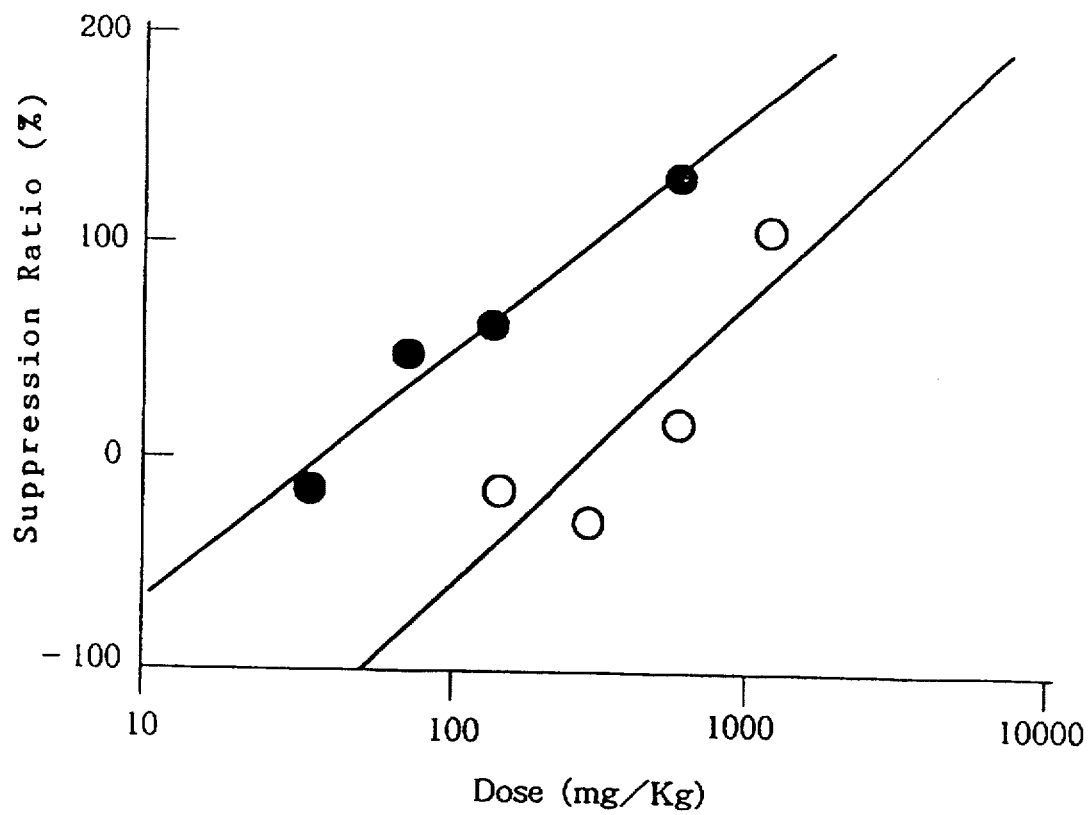
FIG. 1 shows does-response curves of the suppression of increase in cholesterol level wherein closed circles represent the data of the resin of Example 1 while open circles the data of cholestyramine.

To further illustrate the present invention in greater detail and to clarify the effects of the same, the following Examples (Examples and Test Examples) will be given. However, it is to be understood that the present invention is not restricted thereto.

EXAMPLE 1

Into a two-necked flask provided with a reflux condenser and a dropping funnel were introduced 85.9 g (0.6 mol) of acryloyloxyethyl-N,N-dimethylamine, 160 g of acetone and 0.1 g of hydroquinone monomethyl ether, which was employed as a polymerization inhibitor, and then mixed homogeneously. After dropping 75.9 g (0.6 mol) of benzyl chloride into the homogeneous mixture within about 15 minutes, the mixture was allowed to stand overnight under stirring at room temperature. Then the reaction mixture was washed with 500 ml of acetone and thus crystals of acryloyloxyethyl-N,N-dimethylbenzyl ammonium chloride were obtained.

150 g of the crystals of acryloyloxyethyl-N,N-dimethylbenzyl ammonium chloride thus obtained were dissolved in 280 g of purified water in a three-necked separable flask provided with a reflux condenser and the flask was purged with nitrogen for 5 hours. While maintaining the reaction temperature at 65° C., 0.01 g of 2,2'-azobis (2-amidinopropane) hydrochloride was added thereto as a polymerization initiator. After effecting a reaction for about 20 hours, the reaction product was reprecipitated from acetone to thereby give an anion exchange resin.

The thus obtained anion exchange resin was white-colored powder with a slight strange smell. This powder was difficulty soluble in methanol, scarecely soluble in acetonitrile and hygroscopic. The powder was incorporated water, 1N solution of sodium hydroxide and 1N solution of hydrochloric acid to thereby exhibit consistency. An aqueous solution of 50 g/l of this anion exchange resin exhibited a qualitative reaction as a chloride.

The anion exchange resin in the powder form was measured for its purity and found to be very high in purity with the balance being that the residual acetone was not more than 100 ppm, the residual monomer not more than 19 ppm, the residual benzyl chloride not more than 315 ppm, benzyl alcohol not more than 233 ppm, heavy metals not more than 10 ppm, arsenic not more than 1 ppm and a quaternary ammonium salt not more than 3500 ppm.

0.5 g of the acrylic polymer produced in this Example was incorporated with water and then dissolved under agitation to obtain 50 ml of a solution of the resin, after which the solution was measured for pH by HH-50S (Trade Name, produced by TŌA DENSHI Inc.) and found to be 5.4–5.6. Further, 0.25 g of this resin were incorporated with 50 ml of a solution of Food Red No. 3 (2 g/l), agitated 5 minutes and then ultrafilterd to obtain a colorless to slightly red liquid. Then, 0.5 g of this resin were incorporated with 5 ml of a 1N solution of sodium hydroxide and then heated on a water bath to generate therefrom a gas which smelled something like an amine and turned a red litmus paper blue in color when this paper was exposed to the gas.

Figure 2:
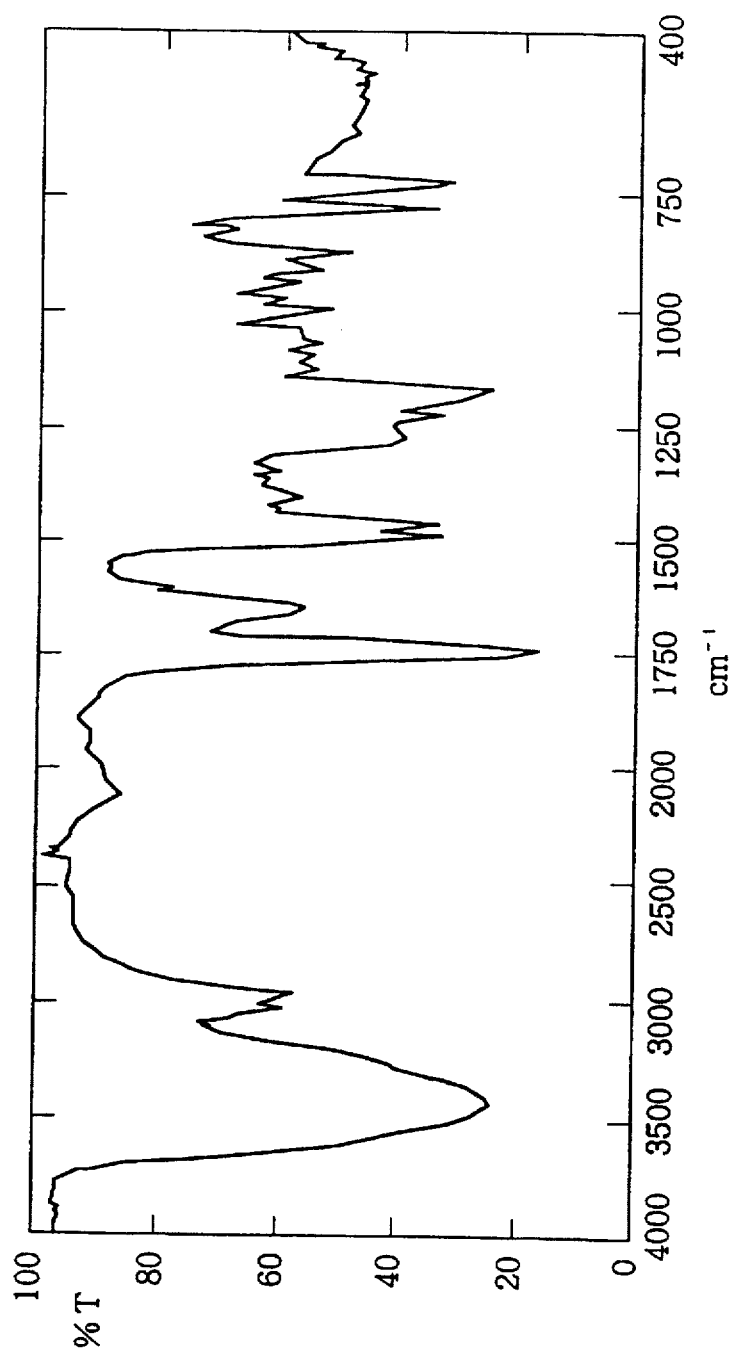
FIG. 2 shows an infrared absorption spectrum of the anion exchange resin of Example 1.

A small quantity of the anion exchange resin of this Example was dried at 80° C. for 8 hours and then measured for its infrared absorption spectrum by a potassium bromide tablet method, with the result that absorptions were found near 3000 $cm^{-1}$, 1735 $cm^{-1}$, 1635 $cm^{-1}$, 1480 $cm^{-1}$, 1200 $cm^{-1}$, 770 $cm^{-1}$ and 715 $cm^{-1}$ of wave number. The results are shown in FIG. 2. Table 2 shows the physical properties of this anion exchange resin other than the above.

Next, a viscosity and weight average molecular weight of the anion exchange resin of Example 1 were measured by the following method and conditions:

<Method for measuring the viscosity>

2.0 g of this compound (the resin) produced in this Example were incorporated with water to form 200 g of a mixture and then agitated for 24 hours to obtain an aqueous solution of the resin. The thus obtained solution was measured for viscosity under the following conditions.

Type of machine: B type viscosimeter (trade name: digital viscosimeter DVM, produced by TŌKYŌ KEIKI Inc.)
Temperature: 25° C.
Number of revolution: 60 r.p.m.
Rotor: No. 2

This anion exchange resin obtained by Example 1 had a viscosity of 102.8 centipoise as measured by a rotary viscosimeter by the above method and conditions.

<Method for measuring the molecular weight>

The weight average molecular weight and average degree of polymerization were measured using GPC (Gel Permeation Chromatography) by the following method and conditions:

The resin produced in this Example was dissolved in a 5 wt. % aqueous solution of sodium hydroxide to obtain a 5 wt. % aqueous solution of the resin. This aqueous solution of the resin was hydrolyzed for a whole day and night at room temperature to convert the resin to a polyacrylic sodium salt in solution. Thereafter, the solution of polyacrylic sodium salt was dialyzed for two days by use of a dialysis membrane which could sieve molecules at a molecular weight of 1000, to completely eliminate the quaternary ammonium salt produced by the hydrolysis from the solution. Then, the thus obtained ammonium salt-free solution was diluted tenfold. The average molecular weight of the polyacrylic sodium salt in the diluted solution was measured under the following conditions. The thus measured average molecular weight of the polyacrylic sodium salt was multiplied by 2.87 to obtain that of said resin.

Detector: RI (differential refractometer)
Column: G6000PWXL-G3000PWXL (trade name, produced by TŌYŌ Soda Inc.)
Column temp.: 40° C.
Mobile phase: 50 mmol/l aqueous solution of sodium chloride
Flow rate: 1 ml/min The weight average molecular weight of the resin of Example 1 measured by means of GPC under the above method and conditions was $372.34 \times 10^4$.

The physical properties of the resin obtained under the conditions of Example 1 are summarized as follows:

pH: about 5.6

Viscosity: 102.8 cP

Weight average molecular weight: $372.34 \times 10^4$

Average degree of polymerization: 13802

EXAMPLE 2

The procedure of Example 1 was followed except that 107.9 g (0.4 mol) of the crystals of acryloyloxyethyl-N,N-dimethylbenzyl ammonium chloride were used, the reaction temperature was 60° C. for 20 hours and a mixture solution containing 91 mg (0.100 mol %) of ammonium persulfate and 42 mg (0.100 mol %) of sodium hydrogen sulfite as a polymerization initiator was used, thereby to obtain an anion exchange resin.

The physical properties of the resin obtained under the conditions of Example 2 are summarized as follows:

pH: 5.3–5.5

Viscosity: 12.4 cP

Weight average molecular weight: $163.26 \times 10^4$

Average degree of polymerization: 6052

As the results of the Infrared adsorption measurements as in Example 1, the same adsortion curves were acknowledged in the resin obtained under the conditions of Example 2.

EXAMPLE 3

The procedure of Example 1 was followed except that 107.9 g (0.4 mol) of the crystals of acryloyloxyethyl-N,N-dimethylbenzyl ammonium chloride were used, the reaction temperature was 50° C. for 20 hours and a mixture solution containing 46 mg (0.050 mol %) of ammonium persulfate and 21 mg (0.050 mol %) of sodium hydrogen sulfite as a polymerization initiator was used, to obtain an anion exchange resin.

The physical properties of the resin obtained under the conditions of Example 3 are summarized as follows:

pH: 5.3–5.5

Viscosity: 29.9 cP

Weight average molecular weight: $248.83 \times 10^4$

Average degree of polymerization: 9224

EXAMPLE 4

The procedure of Example 1 was followed except that 107.9 g (0.4 mol) of the crystals of acryloyloxyethyl-N,N-dimethylbenzyl ammonium chloride were used, the reaction temperature was 40° C. for 20 hours and the mixture solution containing 18 mg (0.020 mol %) of ammonium persulfate and 8.3 mg (0.020 mol %) of sodium hydrogen sulfite as a polymerization initiator was used, to obtain an anion exchange resin.

The physical properties of the resin obtained under the conditions of Example 4 are summarized as follows:

pH: 5.5–5.7

Viscosity: 76.7 cP

Weight average molecular weight: $331.39 \times 10^4$

Average degree of polymerization: 12284

EXAMPLE 5

The procedure of Example 1 was followed except that 107.9 g (0.4 mol) of the crystals of acryloyloxyethyl-N,N-dimethylbenzyl ammonium chloride were used, the reaction temperature was 40° C. for 20 hours and the mixture solution containing 9.1 mg (0.010 mol %) of ammonium persulfate and 4.2 mg (0.010 mol %) of sodium hydrogen sulfite as a polymerization initiator was used, thereby to obtain an anion exchange resin.

The physical properties of the resin obtained under the conditions of Example 5 are summarized as follows:

pH: 5.3–5.5

Viscosity: 109.4 cP

Weight average molecular weight: $378.65 \times 10^4$

Average degree of polymerization: 14036

EXAMPLE 6

The procedure of Example 1 was followed except that 107.9 g (0.4 mol) of the crystals of acryloyloxyethyl-N,N-dimethylbenzyl ammonium chloride were used, the reaction temperature was 40° C. for 20 hours and the mixture solution containing 4.6 mg (0.005 mol %) of ammonium persulfate and 2.1 mg (0.005 mol %) of sodium hydrogen sulfite as a polymerization initiator was used.

The physical properties of the resin obtained under the conditions of Example 6 are summarized as follows:

pH: 5.4–5.6

Viscosity: 135.9 cP

Weight average molecular weight: $480.32 \times 10^4$

Average degree of polymerization: 17805

To illustrate the present invention specifically, the following Test Examples will be given.

Test Example 1

Bile Acid Adsorption Test

The ingredients of a model human bile acid salt composition which are shown in Table 1 were homogeneously mixed and then precisely weighed. 50 ml of purified water, measured accurately, were added thereto to thereby give mixtures corresponding to concentrations of 0.5, 0.6, 0.7, 0.8, 0.9, 1.0, 1.25, 1.5, 1.75, 2.0, 3.0 and 4.0 mM. In each solution, 20 mg of a resin was incubated for 12 hours. Then free bile acids were separated with the use of an ultrafiltration membrane and a membrane filter and the concentration of the free bile acids was measured by an enzymatic method (Bile Acid Test WAKO). Thus the amount of bile acids adsorbed by the resin was calculated and the saturated amount of bile acids adsorbed per unit weight of resin was determined by Langmuir's plotting. Further, the half-saturation concentration and Hill coefficient were determined by Hill's plotting. Thus the affinity for bile acids and synergistic effect of the adsorption sites were determined.

The results determined of the saturated amount of bile acids adsorbed, half-saturation concentration and Hill coefficient of the resin of Example 1 were 5.02 mmol/g, 0.170 mmol/litter and 0.5, respectively.

Similarly, the results of the saturated amount of bile acids adsorbed, half-saturation concentration and Hill coefficient of the resins of Examples 2–6 were almost the same values as the resin of Example 1, respectively.

Moreover, the saturation of adsorption, which can be obtained by Langmuir's plotting, indicates the adsorption capacity of bile acids and it means that the higher numerical value is, the higher the adsorption capacity is. The half-saturation concentration and Hill coefficient can be obtained by Hill's plotting. The half-saturation concentration indicates adsorption affinity for bile acids and it means that the smaller the numerical value is, the higher the adsorption affinity is.

TABLE 1

Model human bile acid salt composition

| Bile acid salt | Amt. (g) | % |
|---|---|---|
| sodium taurocholate | 1.13 | 8.1 |
| sodium glycocholate | 3.28 | 23.4 |
| sodium taurodeoxycholate | 0.74 | 5.3 |
| sodium glycodeoxycholate | 2.91 | 20.8 |
| sodium taurochenodeoxycholate | 1.77 | 12.6 |
| sodium glycochenodeoxycholate | 4.17 | 29.8 |

Test Example 2

Cholesterol Increase Inhibition Test on NZW Rabbits fed with Cholesterol-loaded Feed Using each of the resins of the Examples, a cholesterol increase inhibition test was carried out on NZW male rabbits in the following method.

NZW male rabbits weighing 1.8 kg to 2.3 kg were fed with a standard solid feed containing 0.67% of cholesterol for 1 week. Then the animals were classified into groups in such a manner that the groups were almost identical with one another in the plasma cholesterol level. During the subsequent 2 weeks, each of the resins of Examples 1 to 6 were given in a dose of 500 mg/kg to the rabbits of one specific group everyday. During this period, the standard solid feed containing 0.67% of cholesterol was continuously given at a ratio of 40 g/kg to each of the rabbits. After the end of this period of 2 weeks, the effect of inhibiting the increase in the cholesterol level of each test group was evaluated by calculating the inhibition ratio with respect to the control group (no administration of the test resin). As a control drug, cholestyramine (500 mg/kg) was employed.

The results of the inhibition ratio used the resin of Example 1 and cholestyramine as the control drug were 86.6% and 45.5%, respectively.

Similarly, the results determined of the resins of Examples 2–6 were almost the same values as the resin of Example 1, respectively.

Test Example 3

Single Administration Toxicity Test

Male Wistar-strain rats aged 7 weeks were classified into 5 groups each consisting of 8 animals in such a manner that these groups were almost identical with one another in average body weight. Then the resin of Example 1 dissolved in purified water was administered in doses of 250, 500, 1000, 2000 and 4000 mg/kg to the rats of each of the groups and the acute toxicity was monitored for 2 weeks. Table 2 shows the result including one death case.

TABLE 2

Result of single administration toxicity test

| Dose (mg/kg) | No. of death case/total test cases |
|---|---|
| 4,000 | 1/8 |
| 2,000 | 0/8 |
| 1,000 | 0/8 |
| 500 | 0/8 |
| 250 | 0/8 |

Test Example 4

Test for Dosage to Inhibit Cholesterol Increase, Made on NZW Rabbits Fed with Cholesterol-loaded Feed Using the resin (compound) of Example 1, the test for dosage to inhibit cholesterol increase was made on NZW male rabbits by the following method.

NZW male rabbits weighing 1.8 kg to 2.5 kg were fed with a standard solid feed containing 0.67% of cholesterol for 1 week. Then the animals were classified into groups in such a manner that the groups were almost identical with one another in the plasma cholesterol level. During the subsequent 2 weeks, the resin of Example 1 was given to the rabbits every group in doses of 31.25 mg/kg, 62.5 mg/kg, 125 mg/kg and 500 mg/kg. On the other hand, cholestyramine used as a control drug was given in doses of 125 mg/kg, 250 mg/kg, 500 mg/kg and 1000 mg/kg.

During this period, the standard solid feed containing 0.67% of cholesterol was continuously given at a ratio of 40 g/kg to each of the rabbits.

After 2 weeks, the effect of inhibiting the cholesterol increase of each test group was evaluated by calculating the control ratio with respect to the inhibition group (no administration of the test resin). Thus a dose-response curve was prepared.

The results are shown in Table 3 and FIG. 1.

TABLE 3

Result of dosage-response test of inhibiting cholesterol increase ($ED_{50}$)

| Resin | $ED_{50}$ (mg/kg) |
|---|---|
| resin of Ex. 1 | 98.5 |
| cholestyramine | 549.4 |

Thus it has been found that the resin of Example 1 is about 5.6 times as effective as cholestyramine.

Test Example 5

Reproduction and Development Toxicity Tests (GLP Complied)

The following tests concerning the reproduction and development toxicity (GLP complied) using the compound of Example 1 of the present invention were conducted:

(1) Oral administration test before pregnancy and at the initial stage of pregnancy (rat), (2) Oral administration test at the stage of formation of embryo organs (rat), (3) Oral administration test at the stage of formation of embryo organs (rabbit), and (4) Oral administration test at the stages of periodical parturition period and lactation period (rat).

The results obtained are shown in Tables 4 to 8.

TABLE 4

(Oral administration test before pregnancy and at the initial stage pregnancy: rat)

| Animal species | Administration period and Administration route (number of animals per group) | Dosage (mg/kg) | Results |
|---|---|---|---|
| Rat (Crj:CD(SD) | Male: from 9 weeks before crossbreeding to the end of 2-weeks crossbreeding. Female: from 9 weeks before crossbreeding to the 7th day of pregnacy. Oral administration<br><br>Male: 25 rats per group<br>Female: 25 rats per group | 0<br>100<br>200<br>400 | No effect on the male and female reproduction ability. No fetal effect, growth inhibitory effect, or or malformation inducing effect on embryos. No effect on the reproduction ability of parent animals nor on the development and growth of embryos with a dosage of 400 mg/kg. |

TABLE 5

(Oral administration test at the stage of formation of embryo organs: rat)

| Animal Species | Administration period and Administration route (number of animals per group) | Dosage (mg/kg) | Results |
|---|---|---|---|
| Rat (Crj:CD(SD)) | For 17 days after the 7th day of pregnancy. Oral administration<br><br>Female: 42 rats per group | 0<br>100<br>200<br>400 | No effect on the reproduction ability of female parent animals. No fetal effect on embryos and born animals. No growth inhibitory effect and no malformation inducing effect on embryos and born animals. No effect on the reproduction ability of female parent animals(F0) nor on the development and growth of embryos(F1) with a dosage of 400 mg/kg. No effect on development, growth and reproduction functions of born animals(F1) nor on the development and growth of embryos (F2) with a dosage of 400 mg/kg. |

TABLE 6

(Oral administration test at the stage of formation of embryo organs: rabbit)

| Animal species | Administration period and Administration route (number of animals per group) | Dosage (mg/kg) | Results |
|---|---|---|---|
| Rabbit (Japanese white native species) | For 18 days after the 6th day of pregnancy. Oral administration<br><br>Female: 15 rabbits per group | 0<br>100<br>200<br>400 | No effect on the reproduction ability of female parent animals. Inhibition of an increase in the body weight in a group given 400 mg/kg, and a decrease in food intake. No fetal effect on embryos. No growth inhibitory effect nor malformation inducing effect on embryos. No effect on the reproduction ability of parent female animals nor effect on the development and growth of embryos with a dosage of 400 mg/kg. |

TABLE 7

(Oral administration test at the stage of periodical parturition perod and lactation period: rat)

| Animal species | Administration period and Administration route (number of animals per group) | Dosage (mg/kg) | Results*[1] |
|---|---|---|---|
| Rat (Crj:CD(SD)) | From the 17th day of pregnancy to the 21th day after parturition. Oral administration Female: 25 rats per group | 0<br>100<br>200<br>400 | Difficult parturition was observed in female parent animals.<br>No effect on born animals.<br>No effect on the reproduction ability of female parent animals (F0) with a dosage of 100 mg/kg.<br>No effect on development, growth and reproduction of born animals (F1) nor effect on the development and growth of embryos (F2) with a dosage of 400 mg/kg. |

*[1] See Table 8

TABLE 8

| Items | | Control | 100 mg/kg | 200 mg/kg | 400 mg/kg |
|---|---|---|---|---|---|
| Dead birth of born animals | | 27 | 27 | 40 | 54 |
| Number of survived born animals for 4 days | | 288 | 247 | 238 | 115 |
| Number of born animals that died for 4 days | | 36 | 20 | 71 | 136 |
| Number of died female parent animals | | 0 | 2 | 0 | 1 |
| Number of female parent animals observed to have the following general symptoms*[1] at the beginning of parturition | | 1 | 2 | 3 | 10 |
| Number of female parent animals whose born animals died | Died just after parturition | 0 | 0 | 1 | 2 |
| | Died for 2 days after parturition | 1 | 2 | 6 | 9 |
| Anatomical findings of female parent animals whose born animals all were born dead and of the died female parent animals, and number of said cases | Thymus atrophy | 1 | 1 | 7 | 9 |
| | Adrenal gland hypertrophy | 1 | — | — | 2 |
| | Occurence of ulcer and dark red spots or edematous change in the anterior stomach or duodenum | — | — | — | 5 |

*[1] Standing hair, inhibition of spontaneous motor activity, crouching, blepharoptosis, much bleeding, drop in body temperature, irregular respiration, adhesion of a red secretion around nose.

Test Example 6

Mutagenicity Tests (GLP Complied)

The following tests concerning the mutagenicity (GLP complied) using the compound of Example 1 of the present invention were conducted:

(1) Reverse mutation test on microorganisms, (2) Chromosomal abnormality test on mammalian cultured cells, and (3) Micronucleus test on mice.

The results obtained are shown in Table 9.

Test Example 7

Antigenicity Tests (GLP Complied)

The following tests concerning the antigenicity (GLP complied) using the compound of Example 1 of the present invention were conducted:

(1) PCA (Passive Cutaneous Anaphylaxis) reaction for 48 hours on rats using the ability to produce IgE antibody as indicator, (2) Active systemic anaphylaxis reaction (ASA), and (3) PCA reaction for 4 hours on Guinea pigs using the ability to produce IgG antibody as indicator.

The results obtained are shown in Table 10.

Test Example 8

Ocular Mucosal Primary Irritation Test in Rabbits (GLP Complied)

The following test concerning the Eye mucous membrane primary irritation in rabbit (GLP complied) using the compound of Example 1 of the present invention was conducted.

The results obtained are shown in Table 11.

TABLE 9

(Mutagenicity test (GLP complied))

| Test items | Method | | Results |
|---|---|---|---|
| Reverse mutation test on microorganisms | Strain: | Rat typhus (TA98, TA100, TA1535, TA1537) Coli bacillus WP2uvrA | No observation of reverse mutation mutagenicity. |
| | Method: | Plate method, 48 hours incubation, 2 plates/dosage, 78.125–5000 µg/plate | |
| Chromosomal abnormality test on mammalian cultured cells | Used cells: | CHL cells | No induction of chromosomal abnormalities. |
| | Method: | Direct method treated with 9, 18, 36 µg/ml for 24 hours and 48 hours Metabolism activation method treated with 60, 120, 240 µg/ml for 6 hours | |
| Micronucleous test on mice | Animal: | CD-1 mouse HBS-107 was given orally at a dosage of 500, 1000 or 2000 mg/kg, and a sample was prepared after 24, 48 and 72 hours | No induction of micronucleus formation. |

TABLE 10

(Antigenicity test (GLP complied))

| Test items | Methods | Induced amount (mg/kg) | Results |
|---|---|---|---|
| PCA reaction for 48 hours on rats using the ability to produce IgE antibody as indicator | Animal: Rat (Crj:CD(SD)), 24 males mouse Serum was injected intradermally into the back of rat, and after 48 hours, HBS-107 was injected intravenously into the tail. 30 minutes after the intravenous injection in the tail, the diameter of a colored patch on the skin was measured. | 1 | PCA reaction was not observed by HBS-107. |
| Active systemic anaphylaxis reaction (ASA) | Animal: Guinea pig (Hartley), 24 males 2 weeks after the final sensitization, or the final administration, HBS-107 was injected intravenously and the indication revealed was observed. | 0.5 | ASA reaction was not observed by HBS-107. |
| PCA reaction for 4 hours on Guinea pigs using the ability to produce IgG antibody as indicator | Animal: Guinea pig, (Hartley), 12 males Serum was injected intradermally into the back, and after 4 hours, HBS-107 was injected intravenously. 30 minutes after the intravenous injection, the diameter of a colored patch on the skin was measured. | 0.5 | PCA reaction was not observed by HBS-107. |

TABLE 11

(Ocular mucosal primary irritation test in rabbit (GLP complied))

| Animal species | Method | Results |
|---|---|---|
| Rabbit (Japanese white native species) | No ocular washing group: 5 males Ocular washing group: 3 males 0.1 g sample as ocular-washing was applied to the right eye, and after 4, 24, 48, 72 and 96 hours, the eye was evaluated by visual observation. | The evaluation point of irritation was 23.5 as compared with the theoretical maximum value of 110. The irritation decreased the evaluation point to 18.67 by ocular washing. HBS-107 was found to have irritation which however are not strong. |

Test Example 9

Effect on WHHL Rabbits (1) Method

HBS-107 (compound of Example 1) (500 mg/kg) was administered orally to WHHL male rabbits for 3 months, and their blood was collected on 1, 14, 28, 42, 56, 70, and 84 days after the administration and examined for total cholesterol in serum (n=5).

(2) Results

Figure 3:
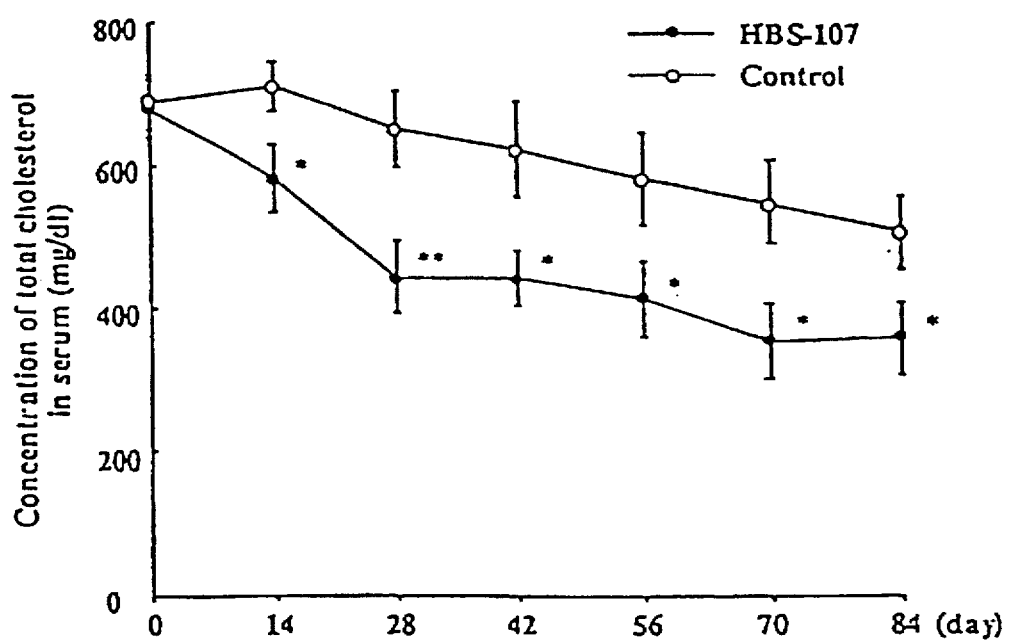
FIG. 3 shows the effect of the compound of Example 1 on the total cholesterol level in rabbits versus controls.

As is apparent from FIG. 3, the compound of Example 1 significantly decreased the total cholesterol in serum.

Note: "Students t test" is one widely known in the art for inspecting significant difference of control drug (HBS-107) to control.

"Control" means data obtained from rabbits of control group which had been bred only by conventional feeds, and "HBS-107" means data obtained from rabbits which had been bred by conventional feeds and control drug (HBS-107).

Test Example 10

Comparison with Cholestyramine in Inhibition on the Excretion of Bile Acid into Bile Duct in Rats (1) Method HBS-107 (compound of Example 1) and cholestyramine were administered orally to SD strain male rats at dosages of 125 mg/kg respectively, and after 3 hours, a cannula was inserted into the bile duct in the animal under urethane anesthesia. Bile was collected continuously for 6 hours, and their excreted bile and total bile acid were determined (n=7 to 8).

(2) Results

The results obtained are shown in Table 12.

As compared with cholestyramine, HBS-107 significantly decreased the excreted bile acid.

TABLE 12

(Inhibition effect of HBS-107 on biliary excretion of bile acid)

| | | Amount of excreted bile acid (µmole) | | difference | % of inhibition |
|---|---|---|---|---|---|
| | n | Average | S.E. | (µmole) | (%) |
| Control | 8 | 63.75 | 2.07 | — | — |
| HBS-107 125 mg/kg | 8 | 39.98 | 1.68 | 24.77 | 38.85* |
| Cholestyramine 125 mg/kg | 7 | 58.06 | 5.38 | 5.69 | 8.93 |

*$p < 0.001$ vs. control, Aspin-Welch t-test

Test Example 11

General Pharmacological Effect

The following tests concerning the General pharmacological effect using the compound of Example 1 of the present invention were conducted:

(1) Effect on the central nervous system
(2) Effect on the circulatory organs
(3) Effect on the smooth muscle
(4) Effect on the digestive organs
(5) Effect on water and electrolytes
(6) Other effect The results obtained are shown in Tables 13 to 18.

TABLE 13

(Effect on the central nervous system)

| Test items | Animal species (Administration route) | Dosage (mg/kg) | Test results |
|---|---|---|---|
| General symptoms | Mouse (p.o.) | 250 500 1000 | No effect |
| Spontaneous motor activity | Mouse (p.o.) | 250 500 1000 | Slight inhibition with a dosage of 1000 mg/kg |
| Pentobarbital anesthesia | Mouse (p.o.) | 250 500 1000 | No effect |
| Fulminating spasm | Mouse (p.o.) | 250 500 1000 | No effect |
| Pentetrazol spasm | Mouse (p.o.) | 250 500 1000 | No effect |
| Normal body temperature | Rabbit (p.o.) | 250 500 1000 | No effect |

TABLE 14

(Effect on the circulatory organs)

| Test items | Animal species (Administration route) | Dosage (mg/kg) | Test results |
|---|---|---|---|
| Respiration, blood pressure, heart rate, electrocardiogram, amount of blood stream | Rabbit (p.o.) | 1000 | No effect |

TABLE 15

(Effect on the smooth muscle)

| Test items | Animal species (Administration route) | Dosage (g/ml) | Test results |
|---|---|---|---|
| Removed ileum | Guinea pig (in vitro) | $10^{-5}$ | Spontaneous motor activity: Contraction reinforcement with at least $10^{-4}$ g/ml |
| | | $10^{-5}$ | |
| | | $10^{-4}$ | Acetylcholine, serotonin contraction: Inhibition with $10^{-3}$ g/ml |
| | | $10^{-3}$ | |
| | | | Histamine, $Ba^{2+}$ contraction: No effect |

TABLE 16

(Effect on the digestive organs)

| Test items | Animal species (Administration route) | Dosage (mg/kg) | Test results |
|---|---|---|---|
| Transport in the intestine | Mouse (p.o.) | 250 | No effect |
| | | 500 | |
| | | 1000 | |
| Gastric liquid secretion | Rat (p.o.) | 250 | Significant inhibition with a dosage of 500 mg/kg |
| | | 500 | |
| | | 1000 | |
| Amount of secreted bile | Rat (p.o.) | 250 | No effect |
| | | 500 | |

TABLE 17

(Effect on water and electrolytes)

| Test items | Animal species (Administration route) | Dosage (mg/kg) | Test results |
|---|---|---|---|
| Urine volume and metabolism of electrolytes | Rat (p.o.) | 30 | No effect |
| | | 100 | No effect |
| | | 300 | No effect |
| | | 1.000 | Significant reduction in urin volume, $Na^+$ and $Cl^-$ |

TABLE 18

(Other effect)

| Test items | Animal species (Administration route) | Dosage (mg/kg) | Test results |
|---|---|---|---|
| Acetic acid writhing | Mouse (p.o.) | 200 | No effect |
| | | 500 | |
| | | 1000 | |

Test Example 12

Test for Toxicity Caused by 52 Weeks-term Repetitive Peroral Ingestion

Using the final compound (the resin) of Example 1, a test for toxicity caused by 52 weeks-term repetitive peroral ingestion was made on 21 Beagle male dogs weighing 6 kg to 10 kg each and aged 4 to 5 month each and on 21 Beagle female dogs weighing 5 kg to 9 kg each and aged 4 to 5 months each by the following method.

The said test animals were classified into five dosage groups (A to E groups), and each animal of each dosage group was dosed with a gelatin capsule exclusively used for test animals (trade name: Type No. 11 (½ oz), produced by TORPAC Ltd.), and filled with a dose of the resin as shown in Table 19, once a day 30 minutes later than a time when the test animal had been fed. This dosage was repeated seven times per week, and was continued in this manner for 52 weeks.

TABLE 19

(Repetitively perorally dosed groups subjected to toxicity test)

| groups | Number of subject animals | | | dosage |
|---|---|---|---|---|
| | Male dogs | Female dogs | Total | (mg/kg) |
| A (control group) | 6 | 6 | 12 | 0 |
| B | 4 | 4 | 4 | 62.5 |
| C | 4 | 4 | 8 | 125 |
| D | 6 | 6 | 12 | 250 |
| E (spare group) | 1 | 1 | 2 | 0 |

After the end of the above dosing, there were made observations and examination such as depilation, vomit containing undigested food, soft feces, diarrhea feces, mucous feces, lacrimation, eye mucus, deposition of plaque, interdigit tumor and other disease, for body weight, electrocadiography, urinalysis, hematologic test, autopsy, organ weight, pathologic test and so on, with the result that no adverse effects were hardly found on any dosed groups dosed with not more than 125 mg/kg, except the group D.

From the above test results of the Test Examples, it is apparent that the pharmaceutical composition according to the present invention is excellent in safety without causing any side effects although it exerts the remarkable effect of the decrease in cholesterol level.

[Industrial Applicability]

The resin (compound) of the present invention has a remarkably high saturability of bile acids adsorbed and is excellent in affinity therefor. Thus it will promote the removal of bile acids when used. In addition, it will exert a remarkable effect of inhibiting an increase in cholesterol level when used. Further, it is a highly safe compound without raising any problems as to toxicity. Therefore the resin of the present invention is effective in lowering cholesterol level and in treating diseases such as atherosclerosis. It can be preferably used as a cholesterol-lowering drug for lowering cholesterol level and is useful as a drug.

We claim:

1. A drug composition containing an effective amount of a non-crosslinked acrylic polymer consisting of polyacryloyloxyethyl-N,N-dimethylbenzyl ammonium salt having a pH of about 4.5 to about 6.5 when 0.5 g of said polymer are dissolved in water to obtain 50 cc of a solution and a viscosity of not higher than about 150 centipoises when said polymer is dissolved in water to form a 1 wt. % aqueous solution at 25° C.

2. A drug composition containing an effective amount of a non-crosslinked anionic exchange resin consisting of polyacryloyloxyethyl-N,N-dimethylbenzyl ammonium salt having a pH of about 4.5 to about 6.5 when 0.5 g of said polymer are dissolved in water to obtain 50 cc of a solution thereof and a viscosity of not more than about 150 centipoises when said polymer is dissolved in water to form a 1 wt. % aqueous solution thereof at 25° C.

3. A drug composition for lowering the cholesterol content of a patient which contains as the main active component a non-crosslinked acrylic polymer according to claim 1.

4. A drug composition for lowering the cholesterol content of a patient which contains as the main active component a non-crosslinked anionic exchange resin according to claim 2.

5. A non-crosslinked acrylic anionic exchange resin which is prepared by reacting $CH_2=CHCOO(CH_2)_2-N(CH_3)_2$ with a benzyl salt of formula $C_6H_5CH_2X$ wherein X is chloride or bromide whereby the quaternary monomer of formula

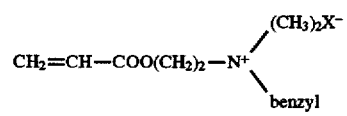

is obtained and then subjecting said quaternary monomer to a free radical polymerization in the presence of a azobisisobutyronitrile (AIBN) or an ammonium/persulfate sodium hydrogen sulfite for a time of from about 0.5 to about 30 hours at a temperature of 15°–80 ° C. to obtain a reaction mixture and precipitating said anion exchange resin by addition of acetone or dioxane to said reaction mixture, said non-crosslinked acrylic anionic exchange resin having a weight average molecular weight between $163.26 \times 10^4$ and $480.32 \times 10^4$ and a viscosity not higher than 150 centipoises and being more effective than cholestyramine in inhibiting cholesterol increase.

6. The anionic exchange resin according to claim 5 which is prepared by
   1) reacting 85.9 g (0.6 mol) of acryloyloxyethyl-N,N-dimethylamine, 160 g of acetone and 0.1 g of hydroquinone monomethyl ether, as a polymerization inhibitor, and after mixing to obtain a homogeneous mixture, adding 75.9 g (0.6 mol) of benzyl chloride to said homogeneous mixture, letting the mixture stand overnight at room temperature, washing the mixture with 500 ml of acetone whereby crystals of the monomer acryloyloxyethyl-N,N-dimethylbenzyl ammonium chloride is obtained;
   2) dissolving 150 g of said crystals of the monomer acryloyloxyethyl-N,N-dimethylbenzyl ammonium chloride in 280 g of purified water, purging with nitrogen for 5 hours;
   3) adding 0.01 g of 2,2'-azobis(2-amidinopropane) hydrochloride while keeping the temperature at 65° C. and letting polymerization to occur for about 20 hours;
   4) precipitating said anion exchange resin by addition of acetone.

7. The anionic exchange resin according to claim 6 wherein said resin has residual acetone content not more than 100 ppm, a residual monomer not more than 19 ppm, residual benzyl chloride not more than 315 ppm, benzyl alcohol not more than 233 ppm, heavy metals not more than 10 ppm, arsenic not more than 1 ppm and said quaternary ammonium salt not more than 3500 ppm.

8. The anionic exchange resin according to claim 7 which has weight average molecular weight of $372.34 \times 10^4$ when measured by Gel Permeation Chromatography and a viscosity of 102.8 centipoises when measured by a rotary viscosimeter.

* * * * *